US008162860B1

(12) United States Patent
Ali

(10) Patent No.: US 8,162,860 B1
(45) Date of Patent: Apr. 24, 2012

(54) MASSAGING SHOE DEVICE

(76) Inventor: Naser Ali, Minneapolis, MN (US)

( * ) Notice: Subject to any disclaimer, the term of this patent is extended or adjusted under 35 U.S.C. 154(b) by 617 days.

(21) Appl. No.: 12/421,511

(22) Filed: Apr. 9, 2009

(51) Int. Cl.
*A61H 1/00* (2006.01)
*A61H 15/00* (2006.01)
*A61F 5/14* (2006.01)

(52) U.S. Cl. .............. 601/115; 36/141; 601/27; 601/28; 601/29; 601/30; 601/112

(58) Field of Classification Search .................... 601/22, 601/27–32, 43, 46, 48–49, 50, 61, 67, 69–70, 601/84, 86–90, 93–95, 97–98, 100, 101, 601/104, 112, 127–129, 133–134, 136, 143–147, 601/DIG. 17, DIG. 14; 36/1, 136–137, 140–144; 15/104.92, 227; 4/605–606
See application file for complete search history.

(56) References Cited

U.S. PATENT DOCUMENTS

| | | | | |
|---|---|---|---|---|
| D281,735 | S | 12/1985 | Seltzer | |
| 5,113,850 | A | 5/1992 | Larremore et al. | |
| 5,592,759 | A | 1/1997 | Cox | |
| 5,836,899 | A | 11/1998 | Reilly | |
| 5,913,838 | A | 6/1999 | Reilly | |
| 6,258,048 | B1 * | 7/2001 | Montague | 601/19 |
| 6,464,654 | B1 | 10/2002 | Montgomery et al. | |
| 2002/0184791 | A1 | 12/2002 | Ko | |
| 2005/0126049 | A1 | 6/2005 | Koenig | |
| 2005/0211270 | A1 * | 9/2005 | Wheelwright | 134/6 |
| 2006/0174522 | A1 | 8/2006 | Yu | |
| 2007/0022632 | A1 | 2/2007 | Lan | |
| 2010/0229884 | A1 * | 9/2010 | Alony | 132/73.5 |

* cited by examiner

*Primary Examiner* — Patricia Bianco
*Assistant Examiner* — George N Phillips

(57) ABSTRACT

A massaging shoe device for providing comfort to a user's feet comprising a base, a hollow foot covering component, a ring-shaped first massaging component disposed inside the foot covering component that can wrap around a users foot, and a second massaging component disposed in the base near the back of the shoe device. The massaging components are for massaging a user's feet.

7 Claims, 5 Drawing Sheets

MASSAGING SHOE DEVICE

FIELD OF THE INVENTION

The present invention is directed to a foot massaging device. More particularly, the present invention is directed to a foot massaging device in the shape of a standard shoe.

BACKGROUND OF THE INVENTION

Foot massages can be very beneficial, particularly after a long day of being on one's feet. The present invention features a massaging shoe device for providing comfort to a user's feet. The massaging shoe device may be constructed to resemble a shoe, and may also be constructed to resemble slippers or other similar shoes.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
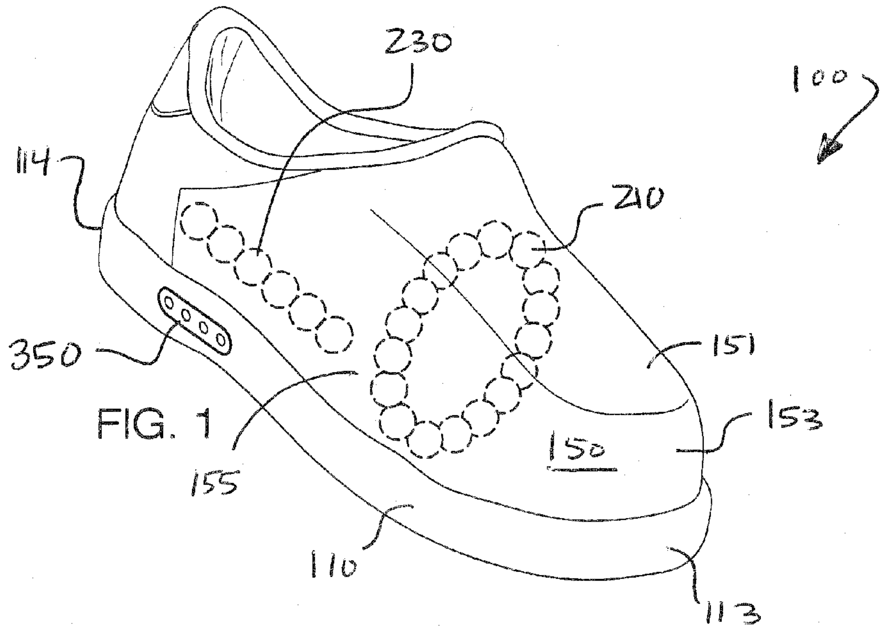
FIG. 1 is a perspective view of the massaging shoe device of the present invention.
Figure 2:
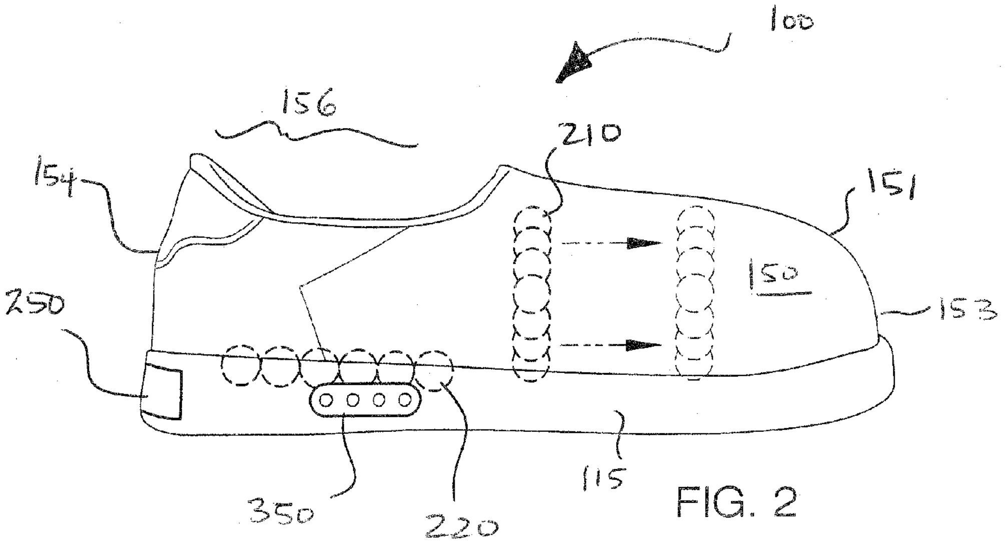
FIG. 2 is a side view of the massaging shoe device of the present invention.
Figure 3:
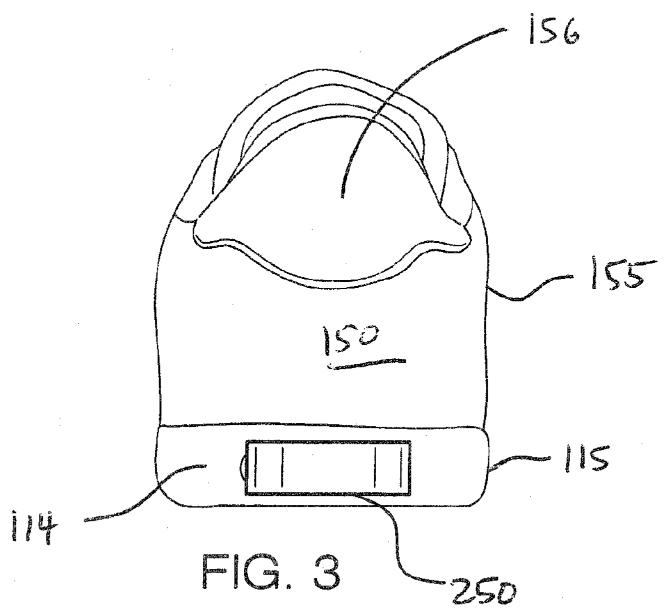
FIG. 3 is a back view of the massaging shoe device of the present invention.
Figure 4:
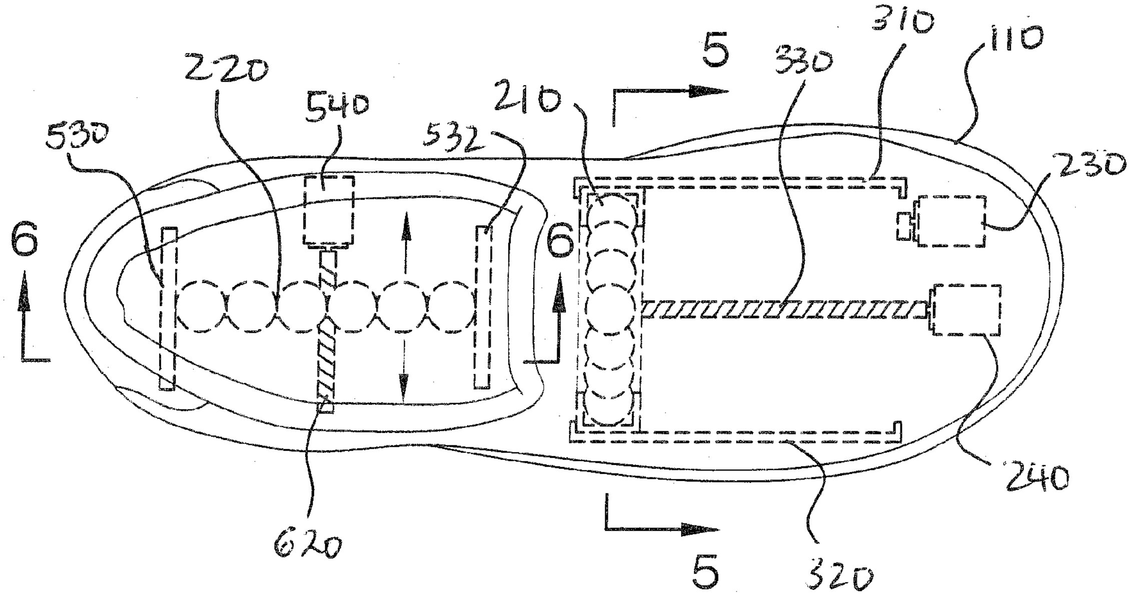
FIG. 4 is a top view and cross sectional view of the massaging shoe device of the present invention.

The following is a listing of numbers corresponding to a particular element refer to herein:

100 massaging shoe device
110 base
111 top surface of base
112 bottom surface of base
113 front edge of base
114 back edge of base
115 side of base
150 foot covering component
151 top of foot covering component
153 front edge of foot covering component
154 back edge of foot covering component
155 side of foot covering component
156 foot hole
210 first massaging component
220 second massaging component
230 vibrating motor
240 movement motor
250 battery compartment
255 battery

310 first rail support
311 first end of first rail support
312 second end of first rail support
320 second rail support
330 firsts screw
350 control switch (e.g., on/off switch)
400 outer ring of massaging component
410 ring of interconnected balls
510 bar
520 interconnected balls on bar
530 track
532 second track
540 gear motor
610 support bar
620 second screw Referring now to FIGS. 1-5, the present invention features a massaging shoe device 100 for providing comfort to a user's feet. The massaging shoe device 100 comprises a base 110 having a top surface 111, a bottom surface 112, a front edge 113, a back edge 114, and a side 115. The base 110 is similar to a standard sole of a shoe (or a slipper) well known to one of ordinary skill in the art.

Attached to the top surface 111 of the base 110 is a hollow foot covering component 150 having a top surface 151, a front edge 153, a back edge 154, a side 155, and an inside surface. The top surface 111 of the base 110 serves as the bottom of the foot covering component 150. Disposed in the top surface 151 of the foot covering component 150 near the back edge 154 is a foot hole 156 for receiving the foot of a user. The foot covering component 150 is similar to a shoe (or a slipper) well known to one of ordinary skill in the art.

Disposed inside the foot covering component 150 is a ring-shaped first massaging component 210. The first massaging component 210 oriented such that a portion of the massaging component 210 is disposed in the base 110, a portion is attached to the top surface 151 of the foot covering component as well as the sides 155 of the foot covering component 150 (see FIG. 1, FIG. 5).

The ring-shaped first massaging component 210 comprises an outer ring 400 having an outer surface, an inner surface, a top edge, a bottom edge, a first side, and a second side. A ring of interconnected balls 410 is attached to the inner surface of the outer ring 400 (see FIG. 5). The interconnected balls 410 are arranged side by side to form a continuous ring. A user can insert his/her foot through the foot hole 156 and through the hollow center of the outer ring 400 such that the ring of interconnected balls 410 wraps around his/her foot.

The first massaging component 210 is designed move forwardly and backwardly, for example forwardly toward the front edge 153 of the foot covering component 150 or backwardly toward the foot hole 156.

The first massaging component 210 is attached to the top surface 111 of the base 110 in between the front edge 113 of the base 110 and the foot hole 156 via a first rail support 310 and a second rail support 320. The rail supports are disposed in the sides 155 of the foot covering component 150. The first rail support 310 and the second rail support 320 are generally flat and rectangular, have a top edge, a bottom edge, a first end, and a second end.

Figure 5:
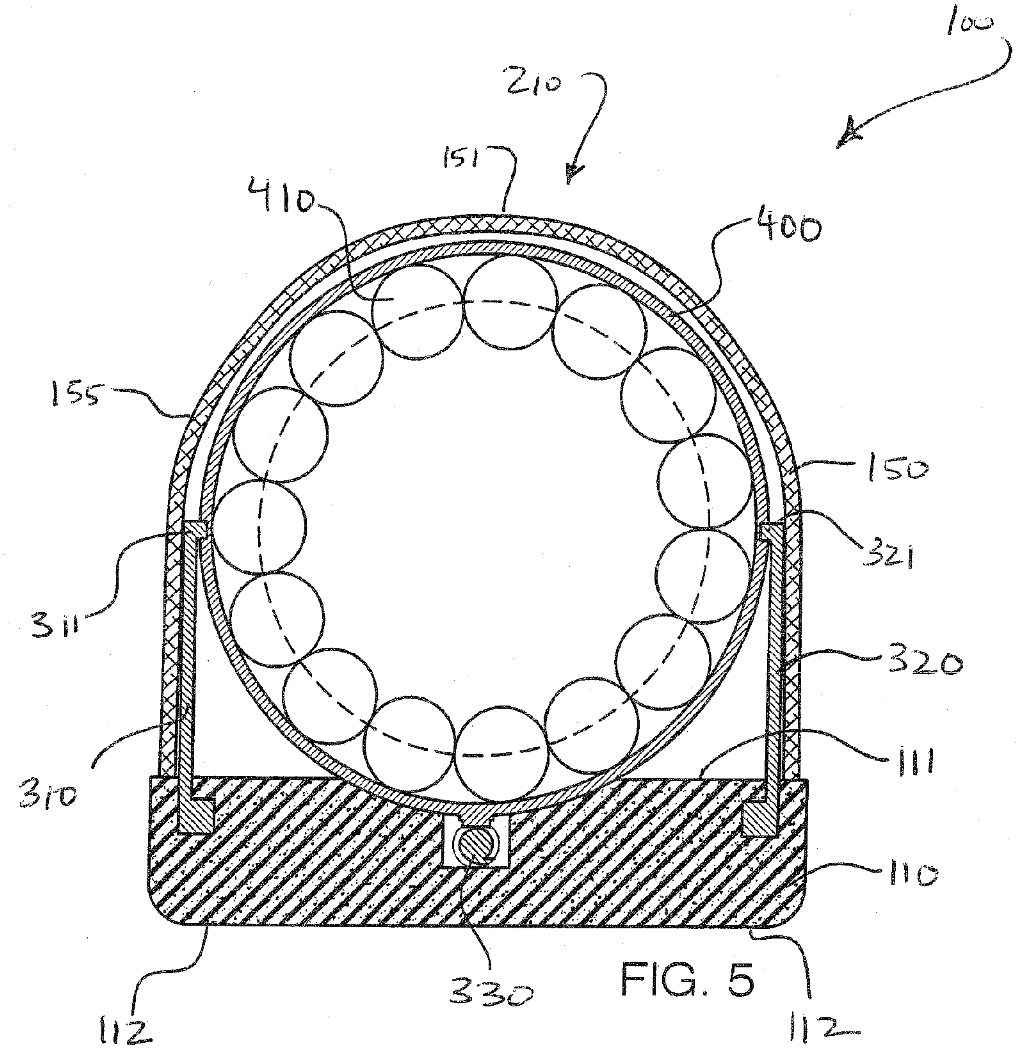
FIG. 5 is a back view and cross sectional view of the massaging shoe device of the present invention.

Disposed on the top edge of the first rail support 310 is a first wing 311 that extends away from the first rail support 310 slightly, inwardly toward the second rail support 310 on the opposite side of the foot covering component 150 (see FIG. 5). Disposed on the top edge of the second rail support 320 is a second wing 321 that extends away from the second rail support 320 slightly, inwardly toward the first rail support 310 on the opposite side of the foot covering component 150. The bottom edges of both rail components are attached to the base 110.

The first wing 311 slidably engages an indentation in the first side of the outer ring 400 and the second wing 321 slidably engages an indentation in the second side of the outer ring 400 of the first massaging component 210. The first massaging component 210 can move forwardly and backwardly, guided by the wings of the first rail support 310 and second rail support 320.

Disposed in the base 110 near the top surface 111 and near the front edge 113 is a first screw 330 that runs along a portion of the length of the base (e.g., length as measured from the front edge 113 to the back edge 114). The first screw 330 has a first end and a second end. The first end of the first screw 330 is attached to a movement motor 240 disposed in the base 110 at the front edge 113. The movement motor 240 causes the first screw 330 to turn in a first direction or a second direction (e.g., clockwise or counterclockwise, respectively). The first screw 330 is threaded through the bottom edge of the outer ring 400 of the first massaging component 210 such that when the first screw 330 is turned by the movement motor 240, the first massaging component 210 moves forwardly or backwardly via the support rails. This allows the interconnected balls 410 to massage move forwardly and backwardly over a user's foot.

In some embodiments, the device 100 of the present invention further comprises a vibrating motor 230 disposed in the base 100. The vibrating motor 230 is electrically/operatively connected to the first massaging component 210 so that the vibrating motor can cause the interconnected balls 410 to vibrate. The vibration of the balls 410 helps to massage the user's foot.

Figure 6:
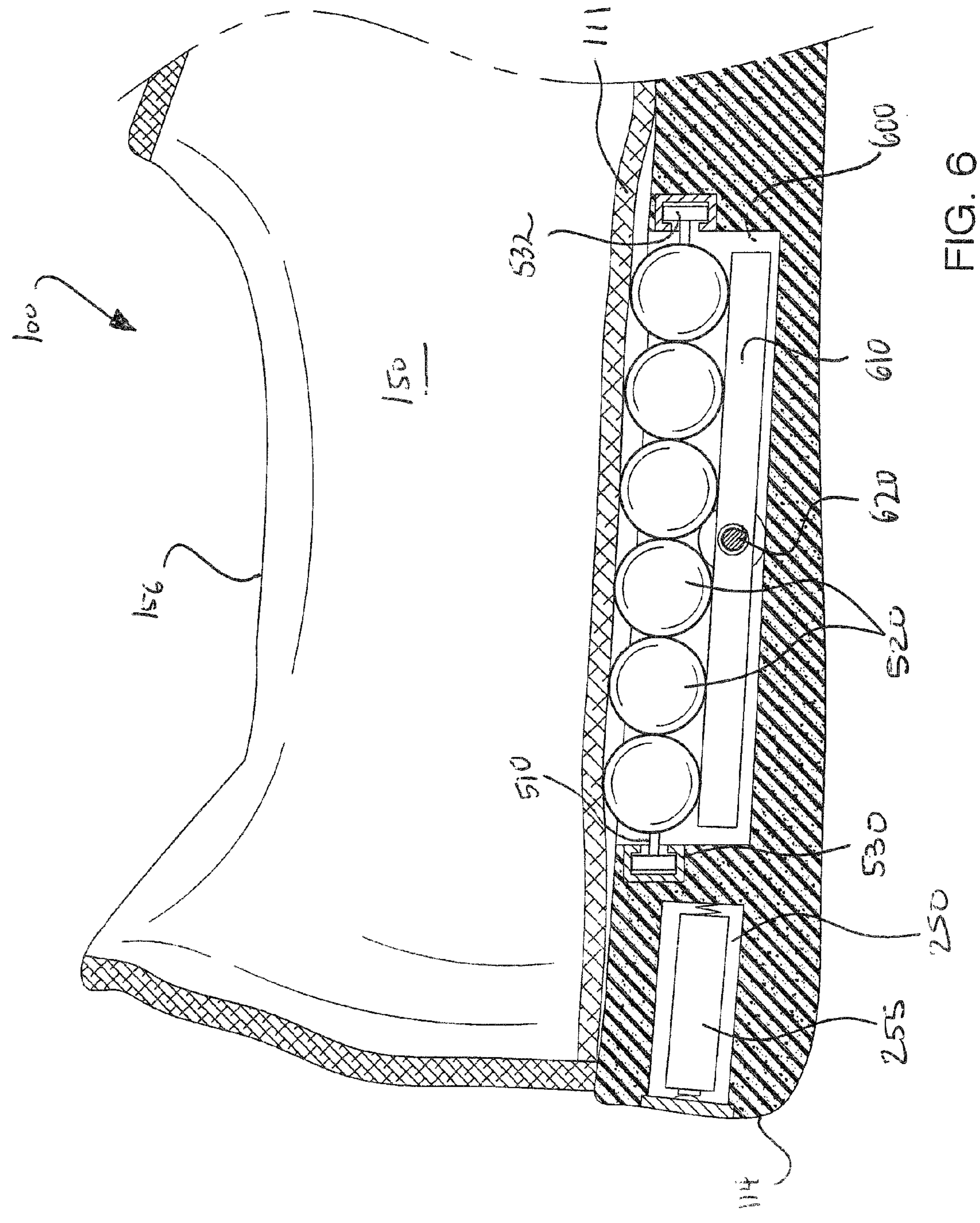
FIG. 6 is a side and cross sectional view of the massaging shoe device of the present invention.
Figure 7:
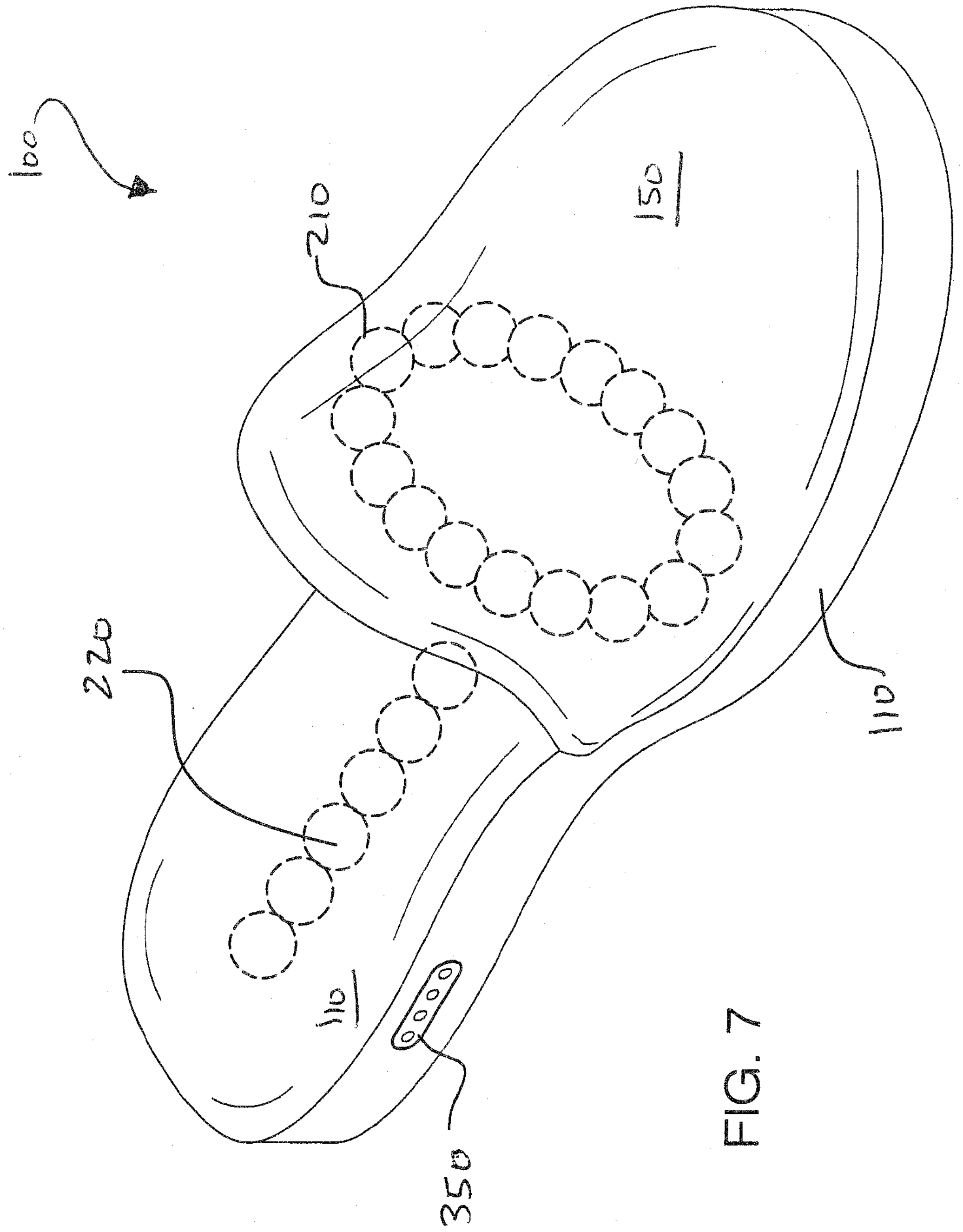
FIG. 7 is a perspective view of an alternative embodiment of the massaging shoe device of the present invention, wherein the shoe device is constructed in the form of a slipper.

Disposed on or near the top surface 111 of the base 110 underneath the foot hole 156 is a second massaging component 220 contained in an inner cavity 600. The second massaging component 220 comprises a thin elongated bar 510 having a first end and a second end. Attached along the length of the bar 510 is a string of interconnected balls 520 (see FIG. 6). In some embodiments, a support bar 610 is attached to the string of interconnected balls 520, for example the support bar 610 is parallel to the bar 510. In some embodiments, the support bar 610 is oriented below the interconnected balls 520.

The first end of the bar 510 is slidably inserted into a first track 530 and the second end of the bar 510 is slidably inserted into a second track 532. The first track 530 is disposed in the base 110 near the back edge 114 and near the top surface 111. The first track 530 extends from near the first side of the base 110 to near the second side of the base 110 (see FIG. 4, FIG. 6). The second track 532 is disposed in the base 110 near the top surface 111. The second track 532 may be disposed in the middle region on the base 110. The second track 523 may be disposed near the front edge 113 of the base 110. The second track 532 extends from near the first side of the base 110 to near the second side of the base 110.

The bar 510 can be moved from side to side (e.g., from near the first side of the base 110 to near the second side of the base 110 and vice versa) within the inner cavity 600 of the base 110 with the first end of the bar 510 connected to the first track 530 and the second end of the bar 510 connected to the second track 532.

Disposed in the inner cavity 600 of the base 110 is a second screw 620 having a first end and a second end. In some embodiments, the first end is oriented near the first side of the base 110 and the second end is oriented near the second side of the base 110. Disposed on the first end of the second screw 620 is a gear motor 540 that turns the second screw 620 in a first direction or a second direction (e.g., counterclockwise, clockwise). The second screw 620 is adapted to engage the support bar 610 below the string of interconnected balls 520. When the second screw 620 is rotated in a first direction or second direction, the support bar 610 (and the interconnected balls 520) is moved from side to side within the base 110 (e.g., from the first side of the base 110 to the second side of the base 110 and vice versa). This allows the string of interconnected balls 520 to massage the user's foot.

In some embodiments, the massaging shoe device (e.g., vibrating motor 230 and/or movement motor 240 and/or gear motor 540) of the present invention is electrically/operatively connected to a power source. For example, in some embodiments, the power source is a battery 255. In some embodiments, the massaging shoe device 100 comprises a battery compartment 250. In some embodiments, the battery compartment 250 is disposed in the base 110, for example near the back edge 114 of the base 110 (see FIG. 3).

In some embodiments, the massaging shoe device 100 of the present invention can be controlled via a control switch 350. For example, in some embodiments, the control switch 350 can be an on/off switch. In some embodiments, a control switch 350 can regulate the speed of the first massaging component 210 and/or second massaging component 220.

The massaging shoe device 100 of the present invention may be constructed from a variety of materials. For example, in some embodiments, the shoe massaging device 100 is constructed from a material comprising a canvas, a leather, a plastic, a rubber, a metal, the like, or a combination thereof. The massaging shoe device 100 of the present invention may be constructed in a variety of sizes to accommodate feet of all sizes and widths. For example, the massaging shoe 100 device may be constructed in sizes for men, women, and children.

The following the disclosures of the following U.S. patents are incorporated in their entirety by reference herein: U.S. Pat. No. 6,464,654 B1; U.S. Pat. No. 5,836,899; U.S. Pat. No. 5,592,759; U.S. Pat. No. 5,113,850; U.S. Pat. No. 5,913,838; U.S. Pat. Application No. 2005/0126049 A1; U.S. Pat. Application No. 2002/0184791 A1; U.S. Pat. Application No. 2007/0022632 A1.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A massaging shoe device for providing comfort to a user's feet, said massaging shoe device comprising:

(a) a base similar in shape to a standard sole of a standard shoe;

(b) a hollow foot covering component attached to a top surface of the base, wherein the foot covering component is similar in shape to a standard shoe well;

(c) a ring-shaped first massaging component disposed inside the foot covering component near a front edge of the foot covering component, wherein the first massaging component comprises an outer ring wherein a ring of interconnected balls is attached to an inner surface of the outer ring;

(d) a first rail support and a second rail support disposed in the foot covering component on a first side and a second side, respectively; wherein a first wing extends from a top edge of the first rail support and a second wing extends from a top edge of the second rail support, wherein the first wing slidably engages a first side of the outer ring and the second wing slidably engages a second side of the outer ring such that the first massaging component can slide forwardly and backwardly along the first rail support and second rail support; and (e) a first screw disposed in the base running along a portion of a length of the base, wherein a first end of the first screw is attached to a movement motor disposed in the base at a front edge of the base; wherein the movement motor causes the first screw to turn in a first direction or a second direction;

wherein the first screw engages a bottom edge of the outer ring of the first massaging component such that when the first screw is turned by the movement motor, the first massaging component moves forwardly or backwardly via the first rail support and second rail support.

2. The massaging shoe device of claim 1 further comprising a second massaging component disposed in an inner cavity in the base near the top surface of the base, said second massaging component comprising:

(f) a thin elongated bar having a string of interconnected balls attached along a length of the bar;

(g) a first track disposed in the base near a back edge for slidably engaging a first end of the bar;

(h) a second track disposed in the base near a middle edge for slidably engaging a second end of the bar;

(i) a second screw having a first end oriented near a first side of the base and a second end oriented near a second side of the base; wherein the second screw engages a support bar attached to a bottom edge of the string of interconnected balls;

(j) a gear motor engaged with the first end of the second screw, wherein the gear motor can rotate the second screw in a first direction and a second direction;

wherein when the second screw is turned by the gear motor, the second massaging component moves between the first side of the base and the second side of the base via the first track and the second track.

3. The massaging shoe device of claim 1, wherein the device further comprises a vibrating motor disposed in the base, wherein the vibrating motor is electrically or operatively connected to the first massaging component so that the vibrating motor can cause the first massaging component to vibrate and massage a user's foot.

4. The massaging shoe device of claim 1, wherein the device comprises a control switch for turning the device on and off.

5. The massaging shoe device of claim 1, wherein the movement motor and gear motor are electrically or operatively connected to a power source.

6. The massaging shoe device of claim 5, wherein the power source is a battery.

7. The massaging shoe device of claim 1, wherein the massaging shoe device comprises a battery compartment disposed in the base.

* * * * *